United States Patent [19]

Speidel

[11] 4,116,217

[45] Sep. 26, 1978

[54] DEFLATION VALVE FOR BLOOD PRESSURE MEASURING DEVICES

[76] Inventor: Blasius Speidel, Hochmeisterstrasse 33, 7455 Jungingen, Fed. Rep. of Germany

[21] Appl. No.: 751,717

[22] Filed: Dec. 17, 1976

[30] Foreign Application Priority Data

Dec. 22, 1975 [DE] Fed. Rep. of Germany ....... 2558058

[51] Int. Cl.² .......................... A61B 5/02; F16K 11/02
[52] U.S. Cl. ............................... 137/625.12; 137/557; 251/321; 128/2.05 G
[58] Field of Search ............... 251/331, 344, 343, 342, 251/345, 347, 349, 353, 354, 145, 318, 319, 320, 321, 340; 137/625.12, 557; 128/2.05 G

[56] References Cited

U.S. PATENT DOCUMENTS

| | | | |
|---|---|---|---|
| 2,027,579 | 1/1936 | DeMooy | 251/344 X |
| 2,704,065 | 3/1955 | Clark | 128/2.05 G |
| 2,854,018 | 9/1958 | Kilmarx, Jr. | 251/343 X |
| 3,954,099 | 5/1976 | Raczkowski et al. | 128/2.05 G |
| 4,013,265 | 3/1977 | Speidel | 128/2.05 G |

*Primary Examiner*—William R. Cline
*Attorney, Agent, or Firm*—Joseph A. Geiger

[57] ABSTRACT

A deflation valve for blood pressure measuring devices having a valve body with a threaded extension surrounded by concentric outlet grooves for slow-deflation and dumping purposes, respectively, in an outwardly facing flat valve seat covered by a flexible valve disc. The valve disc, clamped fast on its inner periphery and held against the valve seat by a spring, has attached to it a sleeve-like control member which can be operated at any point on its periphery by a hand holding the inflation bulb to which the valve is attached.

17 Claims, 4 Drawing Figures

DEFLATION VALVE FOR BLOOD PRESSURE MEASURING DEVICES

BACKGROUND OF THE INVENTION

1. Field of the Invention

The present invention relates to pressure relief valves, and, more particularly, to a manually operable deflation valve for the controlled release of air from a pressurized system, the valve being particularly suitable for use in conjunction with a blood pressure measuring device or sphygmomanometer.

2. Description of the Prior Art

Various manually operable pressure relief valves, adapted for blood pressure measuring purposes, are already known from the prior art in this field. In a standard auscultatory blood pressure test, as suggested by Riva-Rocci and Korotkoff, an inflatable cuff is attached to the limb of the person to be examined, whereupon the cuff is inflated by means of suitable inflating means, until a pressure is reached which lies safely above a level at which the systolic blood pressure would normally be found. The blood pressure test is performed by slowly deflating the measuring cuff, through the controlled release of air from the measuring apparatus or sphygmomanometer, until characteristic pulsating blood circulation noises (the so-called Korotkoff noises) are audible through a stethoscope which is placed over an artery of the limb, for example. The pressure at which these pulsating noises first appear is the systolic blood pressure. In most cases, this pressure is ascertained visually on a manometer or pressure gauge which is connected to the pressurized system. As the pressure inside the measuring cuff is further reduced, through the further gradual release of air from the system, the pulsating blood circulation noise will disappear at a certain pressure level which is representative of the diastolic blood pressure. Once the systolic and diastolic pressure readings have been determined in this manner, the apparatus is completely deflated.

It is important that the final deflation be performed very rapidly, in what is known as the "dumping" of the remaining air pressure. On the other hand, it is extremely important that the rate of deflation of the measuring cuff be controllable very accurately and in precise response to the manual touch control of the air deflation valve. The latter, accordingly, must have a slow-deflation mode of operation and a dumping mode of operation.

In one prior art device, disclosed in U.S. Pat. No. 2,006,878, this dual-mode operation is achieved by arranging the deflation valve in the form of mating male and female threads which, while engaged over a very short thread length, control the slow-deflation mode, the complete disengagement of the threads initiating the dumping mode. In addition to the structural complexity of its parts, this valve has the disadvantage of requiring more than one turn for its operation, necessitating repeated gripping of the valve knob with two fingers.

Another prior art deflation valve is disclosed in U.S. Pat. No. 3,254,671, featuring a simple spring-preloaded disc valve which, for dumping purposes, has a lockable open position. This valve lacks the required sensitivity of fine adjustment in the slow-deflation mode, as a minimal depression of the valve plunger under finger pressure immediately creates a large valve opening. A similar deflation valve, with similar disadvantages, is disclosed in U.S. Pat. No. 3,738,357. In this device, the valve seat and valve plunger are tapered, so that less finger pressure, but longer finger movement is necessary; also, the accidental movement of the valve into the dumping mode is prevented by a special stop.

Still another deflation valve is disclosed in U.S. Pat. No. 3,779,236, where the valve action is provided by a plunger which, by moving radially inwardly against a tubular rubber sleeve, pushes the latter away from the plunger bore, so that air can escape alongside the plunger. A toggle-type lever, operated by a finger, actuates the valve plunger with a special cam configuration which also makes it possible to hold the plunger in a locked open position, for the dumping mode.

Still another prior art deflation valve is disclosed in U.S. Pat. No. 4,013,265. This device features a long, slightly tapered valve plunger which is axially openable, against a spring, by means of a pivotable valve lever. A dumping mode is obtained, when the valve plunger is moved to a position in which bypass channels in the plunger body are exposed. In order to prevent an inadvertant movement of the plunger into the dumping mode, there is provided a threshold in the spring bias which opposes the plunger movement; a detent action holds the valve open for dumping purposes.

To the extent that the various prior art devices mentioned above offer sufficient sensitivity of adjustment during the slow-deflation mode, they are relatively complex in structure and therefore expensive. Several of these valves require more than one finger for their operation, so that the hand which holds the inflation bulb cannot perform the deflation control maneuvers, without releasing the bulb and thereby necessitating assistance with the other hand.

SUMMARY OF THE INVENTION

Underlying the present invention is the primary objective of devising an improved deflation valve for blood pressure measuring devices which is simple in structure, and hence inexpensive to manufacture, and which can be conveniently operated by one finger of that hand which holds the inflation bulb, while offering the required adjustment sensitivity for the slow-deflation mode and a quick evacuation capability, when the air in the system is to be dumped.

The present invention proposes to attain this objective by suggesting an improved deflation valve, adapted for blood pressure measuring devices, which has a valve body with an interior cavity communicating with the pressurized system of the blood pressure measuring device, and, which has an outwardly facing valve seat with one or several outlet ports which are normally covered and closed by a valve member, under the action of a closing spring, the valve member being forcibly removable from its normal closed position by means of a manually actuatable control member which is attached to the valve member.

In a preferred embodiment of the invention, the valve seat occupies an annular surface area surrounding a valve body extension. The valve member, preferably made of a resiliently deformable material, such as rubber, for example, has a disc-shaped portion with a central aperture positioning it in relation to the valve body extension. The latter is preferably a threaded extension, carrying thereon a threaded clamping sleeve with a tubular portion that extends axially as far as the valve member, so as to clamp the latter by its inner peripheral margin against the valve body.

On its distal extremity, the clamping sleeve has an enlarged retaining collar for a compression spring whose opposite end is thereby biased towards the valve member. Between the latter and the compression is preferably arranged a spring collar which has an end face bearing against the valve member. The end face of the spring collar is preferably of such a diameter and orientation that pressure is exerted against the valve member over substantially the entire surface area of the annular valve seat.

The invention further suggests a convenient and extremely simple way of achieving the desired deflation sensitivity and dumping capability by providing separate outlet ports for a slow-deflation air flow rate and a quick-deflation or dumping air flow rate. The deformability of the valve member, in combination with the arrangement of separate outlet ports makes it possible to achieve the desired result in a most simple manner, by arranging the different outlet ports in such a way that the valve member, under slight deformation, gradually exposes the slow-deflation outlet port and, under greater deformation, also exposes the dumping outlet port. The deformability of the valve member also makes it possible to locally clamp the latter against the valve body, as mentioned further above.

By way of a further improvement, the present invention suggests that the outlet ports for slow-deflation and for dumping be arranged in the valve seat as concentric grooves, so that the valve responds identically to a partial movement of its valve member from the valve seat, regardless of where on the valve periphery this movement takes place. The arrangement of concentric outlet grooves in the valve seat also makes it possible to use any suitable number and location of connecting channels between the outlet grooves and a central bore which leads through the valve body. Important is only that the connecting channels to the slow-deflation outlet groove collectively establish a certain slow-deflation flow rate and that the connecting channels leading to the dumping outlet groove collectively establish the desired dumping flow rate. In the latter case, the radial width of the dumping outlet groove may dictate multiple connecting channels, in order to maintain their diameter within that width.

Because the proposed deflation valve can be actuated identically at any point along its periphery, it is particularly suited for direct connection to the mouth of a hand-held inflation bulb. For this purpose, the threaded extension of the valve body serves as a part of the connection. The valve actuating member, preferably a tubular, sleeve-like part, having one end portion connected to the periphery of the valve member, conveniently covers the connection between the valve body and the inflation bulb, while being actuatable with a finger of the hand which holds the bulb. The valve body itself may have a mounting face for the direct attachment of a pressure gauge. The result is a compact assembly of simple construction and pleasing appearance. Alternatively, the valve body may have only a standard hose connection leading to the pressure measuring cuff and/or the pressure gauge.

BRIEF DESCRIPTION OF THE DRAWINGS

Further special features and advantages of the invention will become apparent from the description following below, when taken together with the accompanying drawings which illustrate, by way of example, several embodiments of the invention, represented in the various figures as follows.

DESCRIPTION OF THE PREFERRED EMBODIMENTS

Figure 1:
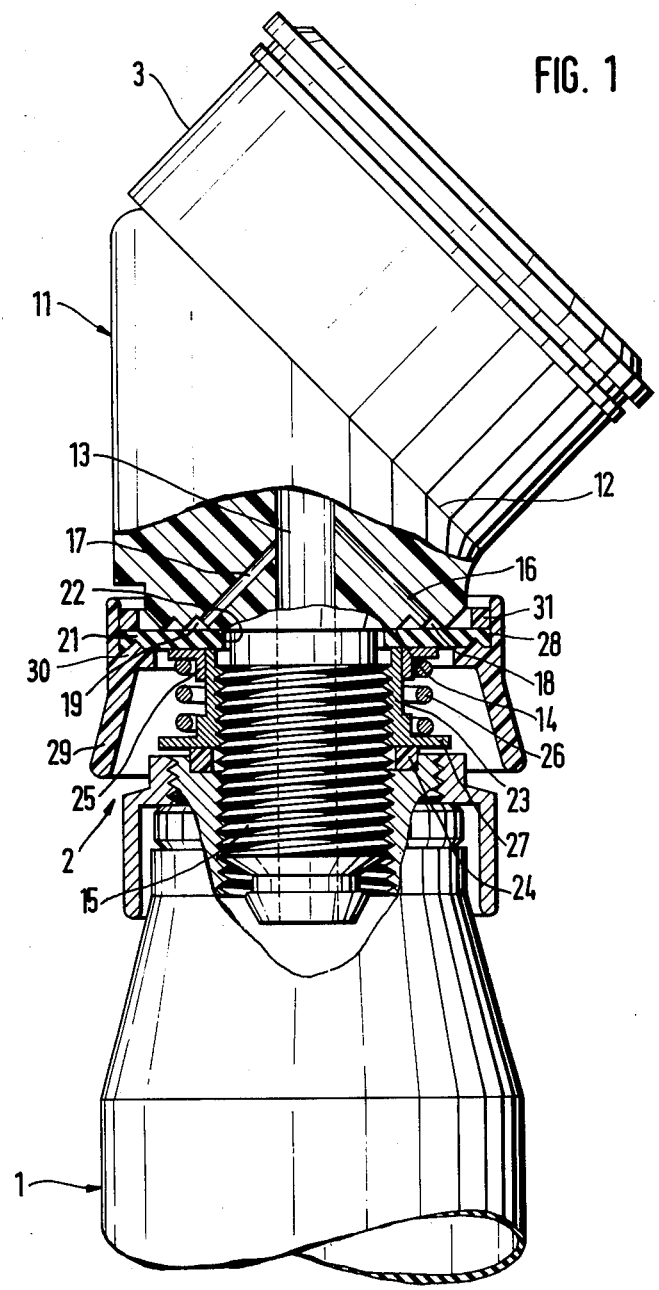
FIG. 1 shows, in partial longitudinal cross section, a first embodiment of a deflation valve for a blood pressure measuring device, having an inflation bulb and a pressure gauge directly attached thereto.

In FIG. 1 of the drawing is illustrated a first embodiment of the deflation valve of the invention, as incorporated in a hand-operated blood pressure measuring device or sphygmomanometer. This device comprises an inflation bulb 1 to the mouth of which is directly attached a deflation valve 2 which, in turn, carries a pressure gauge 3. The conventional pressure measuring cuff and a connecting hose from the valve to the cuff are of well-known design and are therefore not shown. The inflation bulb 1 and the pressure gauge 3 are likewise commercially available components, so that it can be assumed that their internal construction and operation are known.

The deflation valve 2 consists essentially of a valve body 11 with a longitudinal axis defined by a central bore 13 extending through the valve body. On one end, the valve body 11 has an obliquely oriented circular mounting face 12 for the attachment of the pressure gauge 3. The central bore 13 communicates with the latter, and it also leads to an outlet (not shown) for a connecting hose leading to the measuring cuff. The outer end portion of the valve body has the shape of a body of rotation, concentrically surrounding the central bore 13. This shape includes a shoulder configuration between a large diameter and the smaller diameter of a threaded extension 15, the shoulder itself being generally planar in outline and constituting an annular valve seat 14.

To the valve seat 14 lead several diagonal connecting channels, FIG. 1 showing a narrow connecting channel 16 on one side of the central bore 13 and a larger connecting channel 17 on the opposite side of bore 13. At the valve seat 14 itself, the connecting channels 16 and 17 open into two concentrically arranged outlet grooves, the small connecting channel 16, or several such channels, leading to the outer outlet groove, or slow-deflation outlet groove 18, and the larger connecting channel 17, or several such channels, leading to the inner outlet groove, or dumping outlet groove 19. The two outlet grooves 18 and 19 are preferably triangular in cross section. Several connecting channels may be provided for each groove, especially in the case of the dumping outlet groove 19, the diameter of the connecting channels 17 being limited by the width of the dumping outlet groove 19. In the case of the connecting channels 16, it is important that their total flow cross section should not exceed the intended maximum slow-deflation flow rate. Where several connecting channels are provided for an outlet groove, the connecting channels are preferably regularly spaced around its circumference.

The valve seat 14 and its outlet grooves 18 and 19 are covered by a valve member 21 in the form of an annular flat disc. This valve disc is made of a resiliently deformable material, preferably rubber. The valve disc 21 has a central aperture through which extends the externally threaded extension 15 of the valve body 11. An internally threaded clamping sleeve 23 is seated on the threaded extension 15, engaging the valve disc 21 near its periphery, thereby clamping it against the valve body. This means that the valve disc 21 has to undergo a bending deformation, in order to expose one or both outlet grooves in the valve seat 14.

Surrounding the clamping sleeve 23 is a compression spring 26 which is axially confined between a retaining collar 27 at the distal extremity of the clamping sleeve 23 and a movable spring collar 25 which is interposed between the near extremity of the spring 26 and the valve disc 21. The spring collar 25 is longitudinally movable along the outer diameter of the clamping sleeve 23. It engages the valve disc 21 with a face which distributes the spring pressure onto an area of the valve disc 21 which is approximately equal to the surface area of the valve seat 14 on the opposite side of the valve disc 21. The spring 26 and the spring collar 25 thus provide assurance that the valve disc 21 remains safely closed against the valve seat 14, when the valve is in its normal non-operating position.

A control member 29 in the form of a generally tubular sleeve surrounds the valve disc 21, being connected to its outer periphery. This control member 29 has a cylindrical portion extending towards the valve body 11 and an outwardly tapering portion extending towards the inflation bulb 1. Near the extremity of its cylindrical portion, the control member 29 has an inwardly extending flange 30 with which it engages a peripheral portion of the valve disc 11 from one side. The flange 30 and a retaining ring 31, arranged on the opposite side of the valve disc 21, provide the connection between the valve disc and the control member 29. The latter and the retaining ring 31 are preferably plastic parts which are permanently welded or bonded together.

The threaded extension 15 of the valve body 11 not only carries the clamping sleeve 23, but it also serves as a connecting element for the inflation bulb 1. The latter has a mouth portion with a matchingly threaded connecting member, a gasket 24 being interposed between the connecting member and the threaded clamping sleeve 23 of the valve assembly.

The outlet valve of the inflation bulb 1 may be conveniently arranged inside the threaded extension 15, in the central bore 13 of the valve body 11. This valve is preferably a conventional check valve, of the rubber sleeve type, for example, and it is therefore not shown in the drawing.

The outwardly tapering portion of the control member 29, while serving as a cover for the compression spring 26 of the valve 2 and for the connection between the latter and the inflation bulb 1, is that part of the control member which will be engaged by a finger, in order to operate the deflation valve. As can readily be seen in FIG. 1, the position of the control member 29 in relation to the inflation bulb 1 makes it possible for the operator's hand to remain in place around the inflation bulb 1, while one finger of the hand, preferably the thumb, touches the control member 21 to actuate the deflation valve 2. The fact that both the inflation bulb 1 and the operating parts of the deflation valve 2 are round further makes it possible to hold and operate the device without regard to its rotational position, except for the need to be able to read the pressure gauge 3, if the latter is directly attached to the valve body 11.

In order to enhance the effectiveness of the sealing action between the flexible valve disc 21 and the valve seat 14, it is further suggested that the latter not be flat, but that the valve seat surface areas which are located radially outside the outlet groove 18 and between the two outlet grooves 18 and 19 be narrowed to form pointed ridges facing against the valve disc 11, so as to produce an indentation in the latter, under the action of the compression spring 26. While it is the outermost ridge formation which must provide the sealing action, the ridge profile between the two outlet grooves is the necessary result of arranging two grooves of triangular cross section at a minimal radial spacing.

Figure 2:
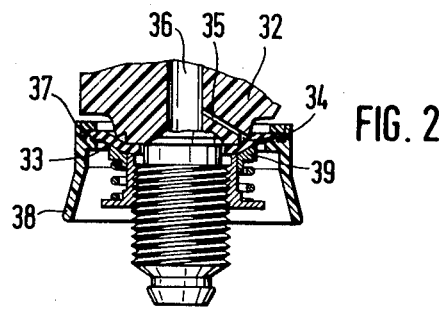
FIG. 2 shows a portion of FIG. 1 with modified deflation valve components.

In FIG. 2 is shown a second embodiment of the invention which is outwardly similar to the first embodiment just described, except for certain modifications in the shape of the valve seat and cooperating elements of the valve.

The valve body 32, rather than having a planar valve seat, has a valve seat 33 of conical outline. While FIG. 2 shows only a single outlet groove 34 and a single connecting channel 35, it should be understood that this is merely a device for simplifying the drawing and that the statements made further above in regard to the preferred arrangement of two concentric outlet grooves and multiple connecting channels also apply to this embodiment. The valve disc 37 is no longer flat, but has a conical shape matching that of the valve seat 33. However, at least the outer peripheral portion of the valve disc 37 is planar in orientation, for attachment to the control member 38. The latter is substantially unchanged from the previous embodiment.

The clamping sleeve and the compression spring of this embodiment are the same as in the previously described embodiment. However, the spring collar 39 which is interposed between the compression spring and the valve disc 37 has a conical end face, in order to again distribute the spring pressure over an area of the valve disc which corresponds to approximately the surface area of the valve seat 33 on the opposite side of disc 37. The arrangement of a conical valve seat makes it possible to choose a steeper orientation of the connecting channels 35 between the outlet grooves 34 and the central bore 36 of the valve body 32. This makes for shorter connecting channels.

Figure 3:
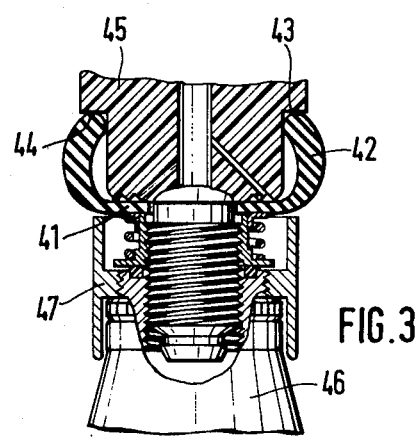
FIG. 3 shows a different deflation valve, representing another embodiment of the invention.

In FIG. 3 is shown a third embodiment of the invention, where the valve seat is again planar in orientation and the valve body 45 is the same as in the embodiment of FIG. 1, except for a cylindrical valve body portion which adjoins the valve seat and terminates at a radial shoulder 44. The valve disc 41, rather than being a flat disc connected on its periphery to a control member, is combined with the control member 42 in the form of a cup-shaped integral part of deformable material, preferably rubber.

The control member 42 or side wall of the cup-shaped part has a somewhat heavier wall, with which it is engaged over the cylindrical portion of the valve body 45. This heavier wall, however, has a radially outwardly arched cross section. As any part of the arched control member 42 is radially depressed and flattened against the cylindrical valve body portion, the attached flat bottom, i.e. the valve disc 41, is pushed axially away from the valve seat, while the rim 43 on the opposite extremity of the control member 42 abuts against the shoulder 44 of the valve body 45. Here again, the deflation valve responds identically to finger touch at any point on its periphery.

The threaded valve body extension, the clamping sleeve, the compression spring, and its spring collar, are substantially the same as in the embodiment of FIG. 1. A protective collar 47 covers the connection between the inflation bulb 46 and the threaded extension of the valve body 45.

Figure 4:
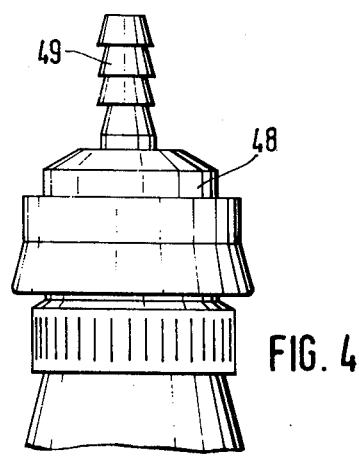
FIG. 4 is an outside view of a modified deflation valve with an exterior hose connection for the pressure gauge and measuring cuff.

A fourth embodiment of the invention, shown in FIG. 4, shows a valve body 48 of modified shape, for direct connection to an air hose by means of a suitable connecting nipple 49. In this case, the pressure gauge is not a part of the hand-held assembly. It may be arranged either on the measuring cuff itself, or somewhere inbetween the measuring cuff and the deflation valve. With the exception of the modified valve body 48, the structure of the deflation valve of this embodiment may be the same as that shown in FIG. 1, or FIG. 2, for example.

It should be understood, of course, that the foregoing disclosure describes only preferred embodiments of the invention and that it is intended to cover all changes and modifications of these examples of the invention which fall within the scope of the appended claims.

I claim the following:

1. A manually operable deflation valve for the adjustable slow release of air from a pressurized air system and for the selective quick deflation of said system, which is particularly suited for use in conjunction with a blood pressure measuring device, for example, the valve comprising in combination:
   a valve body enclosing a cavity in communication with said pressurized air system and defining a valve axis;
   a valve seat arranged on the outside of the valve body, on a surface area of the latter which faces outwardly in a substantially axial direction and surrounds an axial protrusion of the valve body;
   at least one outlet port to the atmosphere arranged within the surface area of the valve seat, and at least one connecting channel leading from the valve body cavity to said outlet port;
   a valve member mounted on the valve body so as to cooperate with its valve seat in such a way that, in its normal position, it covers and closes said outlet port, or ports, to the atmosphere, the valve member being forcibly removable from said normal position into a position in which air can flow through said outlet port, or ports, respectively;
   means for guiding and positioning the valve member in relation to the valve body, said means being defined by the valve body and by a peripheral portion of the valve member surrounding a valve member aperture accommodating said valve body protrusion;
   spring means biasing the valve member towards its normal position; and
   a manually adjustably actuatable control member connected to the valve member in such a way that, when actuated, it effects said forcible removal of the valve member from the valve seat in proportion to the displacement of the control member.

2. A deflation valve as defined in claim 1, wherein the aperture of the valve member and the valve body protrusion have matching circular contours with which they constitute said valve member guiding and positioning means; and
   the surface area of the valve seat is an annular area defined by an axial shoulder of the valve body surrounding said valve body protrusion.

3. A deflation valve as defined in claim 1, wherein the valve member guiding and positioning means includes a round extension on the valve body and a matching circular aperture of the valve member;
   the valve member is made of resiliently deformable material, having an annular disc-shaped portion surrounding said extension and engaging the valve seat in the manner of a lid, the disc-shaped portion being deformable, so as to expose a progressively increasing surface area of the valve seat, as the valve member is forcibly removed from its normal position; and
   the valve member is clamped against the valve body on its inner peripheral margin.

4. A deflation valve as defined in claim 3, wherein the valve body protrusion is a generally cylindrical extension;
   the spring means includes a compression spring surrounding said extension, the spring having its distal end supported by a retaining collar on said extension, in such a way that its near end exerts a bias against the valve member; and
   the spring means further includes a spring collar arranged between the near extremity of the compression spring and the valve member, the spring collar engaging the valve member with an end face whose dimensions and orientation are such that said disc-shaped portion of the valve member is pressed against the valve seat over at least a major portion of the enclosed area of the latter.

5. A deflation valve as defined in claim 4, wherein the valve body extension has a threaded length portion, carrying thereon a threaded clamping sleeve;
   the clamping sleeve includes said spring retaining collar as part thereof and has a tubular portion occupying a radial space between the valve body extension and the compression spring; and
   the clamping sleeve further has a radially narrow axial end face pressing the inner peripheral margin of the valve member against the valve body, thereby providing said valve member clamping action.

6. A manually operable deflation valve for the adjustable slow release of air from a pressurized air system and for the selective quick deflation of said system, which is particularly suited for use in conjunction with a blood pressure measuring device, for example, the valve comprising in combination:
   a valve body enclosing a cavity which is in communication with said pressurized air system;
   an outwardly facing valve seat arranged on the outside of the valve body and occupying a predetermined surface area of the latter;
   a plurality of outlet ports to the atmosphere arranged within the surface area of the valve seat, and a plurality of associated connecting channels leading from the valve body cavity to said outlet port;
   a valve member mounted on the valve body so as to cooperate with its valve seat in such a way that, in its normal position, it covers and closes the outlet ports to the atmosphere, the valve member being forcibly removable from said normal position into a position in which air can flow through the outlet ports;

spring means biasing the valve member towards its normal position; and a manually adjustably actuatable control member connected to the valve member in such a way that, when actuated, it effects said forcible removal of the valve member from the valve seat in proportion to the displacement of the control member; and wherein said outlet ports and associated connecting channels include at least one port and channel combination whose flow-controlling cross section is comparatively small, for a slow-deflation flow rate therethrough, if said slow-deflation outlet port is exposed by the valve member, said outlet ports and associated connecting channels also include at least one port and channel combination whose flow-controlling cross section is comparatively large, for a quick-deflation or "dumping" flow rate therethrough, if said dumping outlet port is exposed by the valve member; and said slow-deflation and dumping outlet ports are so arranged in relation to the valve member that the latter, when only partially removed from its normal valve seat covering position, exposes only the slow-deflation outlet port, and, when further removed from said position, also exposes the dumping outlet port.

7. A deflation valve as defined in claim 6, wherein the valve seat has a generally circular outer periphery;

the valve member is made of a resiliently deformable material, having a panel portion of substantially uniform wall thickness covering the valve seat in the normal valve member position, said panel portion of the valve member being bendable, as a way of partially removing the valve member from the valve seat, so as to initially expose only the slow deflation outlet port.

8. A deflation valve as defined in claim 7, wherein the valve seat has an annular surface area;

the valve member is clampingly retained against the valve body in a central area which is surrounded by the valve seat;

the control member has a shape which is derived, at least in that part which is connected to the valve member, from a body of rotation, the control member being connected to the valve member on a circle which is located near the outer periphery of the valve member; and the slow-deflation outlet port has the form of a concentric slow-deflation outlet groove in the valve seat, and the dumping outlet port has the form of a concentric dumping outlet groove in the valve seat, with the result that the control member is manually actuatable in identical fashion from any point on its periphery, to first remove the valve member from a first portion of the valve seat in which it exposes a portion of the slow-deflation outlet groove and to subsequently remove the valve member from a second portion of the valve seat in which it also exposes a portion of the dumping outlet groove.

9. A deflation valve as defined in claim 8, wherein the slow-deflation outlet groove is linked to the valve body cavity by a plurality of small connecting channels, having collectively a comparatively small flow-controlling cross section; and the dumping outlet groove is similarly linked to the valve body cavity by a plurality of larger connecting channels, having collectively a comparatively much larger flow-controlling cross section.

10. A deflation valve as defined in claim 9, wherein said small and large connecting channels are spaced at regular angular intervals in relation to their associated outlet grooves.

11. A deflation valve as defined in claim 8, wherein the slow-deflation outlet groove in the valve seat is located radially outside the dumping outlet groove; and the valve seat includes, at least radially outside the slow-deflation outlet groove, a concentric sealing ridge with a pointed edge which cooperates with the deformable valve member in its normal position to produce a circular sealing indentation therein.

12. A deflation valve as defined in claim 8, wherein the control member is an integral peripheral formation of the valve member.

13. A deflation valve as defined in claim 8, wherein the valve body has a body portion whose shape is derived from a body of rotation, having a generally radially facing peripheral surface adjoining a generally axially oriented end face on which the valve seat is arranged;

the control member is a resiliently deformable annular member which is supported on said peripheral surface and connected to the outer periphery of the valve member; and the cross section of the control member includes a radially outwardly arched portion which, when depressed and flattened in the radial sense, causes a connected peripheral portion of the valve member to be removed axially from the valve seat.

14. A deflation valve as defined in claim 13, wherein the peripheral surface of the valve body is a cylindrical surface, and the adjoining end face is a planar surface; and the control member and the valve member are integrally connected to form a cup-shaped part.

15. A deflation valve as defined in claim 8, wherein the valve body has a generally cylindrical threaded extension in the rotational axis defined by the annular valve seat;

the valve member is a valve disc with a central aperture for said extension;

the threaded extension carries a threaded clamping sleeve whose near axial extremity engages the inner periphery of the valve disc, thereby providing said clamping action;

the spring means includes a helical compression spring surrounding the clamping sleeve, a retaining collar at the distal extremity of the latter biasing the spring axially towards the valve disc, where a spring collar is interposed between the spring extremity and the valve disc to distribute the spring pressure over an area of the valve disc which corresponds substantially to the area of the valve seat; and the control member is a generally tubular control sleeve, enclosing within it the valve disc, the clamping sleeve, and the spring, the valve disc being peripherally attached to the control sleeve, near one axial extremity of said sleeve.

16. A deflation valve as defined in claim 15, wherein the threaded extension of the valve body is long enough to also serve as part of a rigid threaded connection between the valve body and a hand-held inflation bulb;

the tubular control sleeve has an outwardly tapering sleeve portion covering at least a portion of said connection, while making it possible for a finger of an inflation-bulbholding hand to actuate the control sleeve.

17. A deflation valve as defined in claim 16, wherein the threaded extension has a central bore therethrough, connected on one end with the valve body cavity and connectable on the other end to the interior of said inflation bulb, said bore being adapted to accommodate a check valve; and the valve body further includes a face for the direct attachment thereto of a pressure gauge.

* * * * *